(12) United States Patent
Li et al.

(10) Patent No.: US 11,077,321 B2
(45) Date of Patent: Aug. 3, 2021

(54) METHOD AND SYSTEM OF CONTROLLING MULTI-LEAF COLLIMATOR

(71) Applicant: OUR UNITED CORPORATION, Shaanxi (CN)

(72) Inventors: Jinsheng Li, Shaanxi (CN); Mengmeng Zhang, Shaanxi (CN)

(73) Assignee: OUR UNITED CORPORATION, Shaanxi (CN)

( * ) Notice: Subject to any disclaimer, the term of this patent is extended or adjusted under 35 U.S.C. 154(b) by 0 days.

(21) Appl. No.: 16/598,864

(22) Filed: Oct. 10, 2019

(65) Prior Publication Data

US 2020/0038686 A1 Feb. 6, 2020

Related U.S. Application Data

(63) Continuation of application No. PCT/CN2017/079913, filed on Apr. 10, 2017.

(51) Int. Cl.
*A61N 5/10* (2006.01)
(52) U.S. Cl.
CPC .......... *A61N 5/1048* (2013.01); *A61N 5/1045* (2013.01); *A61N 5/1075* (2013.01); *A61N 2005/1074* (2013.01)
(58) Field of Classification Search
CPC .......... A61N 5/1045–1047; A61N 5/10–1084; A61N 2005/1085–1098
See application file for complete search history.

(56) References Cited

U.S. PATENT DOCUMENTS

| 6,546,073 B1 | 4/2003 | Lee |
| 2007/0041500 A1 | 2/2007 | Olivera et al. |
| 2013/0070898 A1* | 3/2013 | Stahl .................... A61N 5/1068 378/65 |

FOREIGN PATENT DOCUMENTS

| CN | 101267767 A | 9/2008 |
| CN | 103845816 A | 6/2014 |

(Continued)

OTHER PUBLICATIONS

International Search Report and Written Opinion for Application No. PCT/CN2017/079913 dated Jan. 5, 2018. (English Translation).

(Continued)

*Primary Examiner* — Thaddeus B Cox
(74) *Attorney, Agent, or Firm* — Marshall, Gerstein & Borun LLP

(57) ABSTRACT

A method and system of controlling a multi-leaf collimator, wherein steps of the method includes: receiving treatment data, and the treatment data includes position information of N treatment points, conformal position information of N treatment points and radiation field shapes of N treatment points; controlling a treatment head to a conformal position of a first treatment point, and controlling the multi-leaf collimator to begin to conform to a radiation field shape of the first treatment point so as to start a treatment of the first treatment point; controlling the treatment head to a conformal position of a Kth treatment point, and controlling the multi-leaf collimator to begin to conform to a radiation field shape of the Kth treatment point so as to start a treatment of the Kth treatment point; carrying out the described operations repeatedly until the conformation of the radiation field shape and the treatment of all treatment points are completed.

12 Claims, 4 Drawing Sheets

(56) References Cited

FOREIGN PATENT DOCUMENTS

| | | |
|---|---|---|
| CN | 203634645 U | 6/2014 |
| CN | 204134059 U | 2/2015 |
| CN | 104759038 A | 7/2015 |
| CN | 205656865 U | 10/2016 |
| GB | 2370745 A | 7/2002 |
| WO | WO-2005018742 A1 | 3/2005 |

OTHER PUBLICATIONS

Office Action in corresponding Chinese patent application No. 201780003754.4, dated Oct. 9, 2019.
Office Action in corresponding Chinese patent application No. 201780003754.4, dated Apr. 22, 2020.

* cited by examiner

METHOD AND SYSTEM OF CONTROLLING MULTI-LEAF COLLIMATOR

CROSS-REFERENCE TO RELATED APPLICATION

This application is a Bypass Continuation Application of PCT/CN2017/079913 filed Apr. 10, 2017, the entirety of it is incorporated herein by reference.

TECHNICAL FIELD

The present disclosure relates to the field of radiotherapy devices, and in particular, to a method and a system of controlling a multi-leaf collimator.

BACKGROUND

In the field of modern radiotherapy, multi-leaf collimators (MLCs) are important devices for precise radiotherapy. A closed shape conforming to a shape of a patient's lesion may be formed by the independent movement of each leaf of the multi-leaf collimator. In a case where a radiotherapy device emits beams, the closed shape of the multi-leaf collimator constrains the shape of the beams to accurately complete a treatment according to a treatment plan generated by a treatment plan system, which ensures that normal tissues of the patient are protected from excessive radiation, so that the patient may receive a safer and more effective radiation therapy.

SUMMARY

One technical solution adopted by the present disclosure is to provide a method of controlling a multi-leaf collimator, and the method includes: receiving treatment data, and the treatment data includes position information of N treatment points, conformal position information of N treatment points and radiation field shapes of N treatment points, wherein N is a positive integer greater than 1; controlling the treatment head including the multi-leaf collimator to a conformal position of a first treatment point, and controlling the multi-leaf collimator to begin to conform to a radiation field shape of the first treatment point so as to start a treatment of the first treatment point; the conformal position of the first treatment point is between a position of a last treatment point and a position of the first treatment point, or, the conformal position of the first treatment point is at the position of the first treatment point; controlling the treatment head including the multi-leaf collimator to rotate to a conformal position of a Kth treatment point, and controlling the multi-leaf collimator to begin to conform to a radiation field shape of the Kth treatment point so as to start a treatment of the Kth treatment point; wherein $2 \leq K \leq N$, K is a positive integer; carrying out the described operations repeatedly until the conformation of the field shape and the treatment of all treatment points are completed; the conformal position of the Kth treatment point is between a position of a (K−1)th treatment point and a position of the Kth treatment point.

Another technical solution adopted by the present disclosure is to provide a system of controlling the multi-leaf collimator, including a processor, and the processor is configured to: receive treatment data, and the treatment data includes the position information of the N treatment points, the conformal position information of the N treatment points and the radiation field shapes of the N treatment points, wherein the N is a positive integer greater than 1; control the treatment head including the multi-leaf collimator to rotate; control the multi-leaf collimator to begin to conform to the radiation field shape of the first treatment point so as to start the treatment of the first treatment point in a case where the treatment head is controlled to rotate to the conformal position of the first treatment point; the conformal position of the first treatment point is between the position of the last treatment point and the position of the first treatment point, or, the conformal position of the first treatment point is at the position of the first treatment point; control the multi-leaf collimator to begin to conform to the radiation field shape of the Kth treatment point so as to start the treatment of the Kth treatment point in a case where the treatment head is controlled to rotate to the conformal position of the Kth treatment point; wherein $2 \leq K \leq N$, K is a positive integer; the conformal position of the Kth treatment point is between the position of the (K−1)th treatment point and the position of the Kth treatment point.

DETAILED DESCRIPTION

The technical solutions of the present disclosure will be further described in detail below in combination with specific embodiments. Obviously, the described embodiments are merely some but not all of embodiments of the present disclosure. All other embodiments obtained by a person of ordinary skill in the art without paying any creative effort on the basis of the embodiments of the present disclosure shall all be included in the protection scope of the present disclosure.

In the related art, the treatment head is a key component of the radiotherapy device, and the treatment head includes a radiation source and a multi-leaf collimator. The radiation source may emit radiation that treats the lesion, and the multi-leaf collimator may conform the lesion to form a closed shape that matches the shape of the lesion.

However, if continuous treatment is required for multiple treatment points, schemes in the related art often has a situation in which the treatment process of the radiation source is not synchronized with the conformation process of the multi-leaf collimator, that is, in the related art, during the treatment process between two adjacent treatment points, the conformation of the multi-leaf collimator remains consistent with the shape of the lesion at the location of the previous treatment point, and during the treatment between adjacent treatment points, the shape of the lesion changes due to the patient's breathing, involuntary movement, etc., which result in a larger treatment error in a case where the patient is treated with the relevant technology, thereby causing greater radiation damage to the normal tissue surrounding the patient's lesion.

Figure 1A:
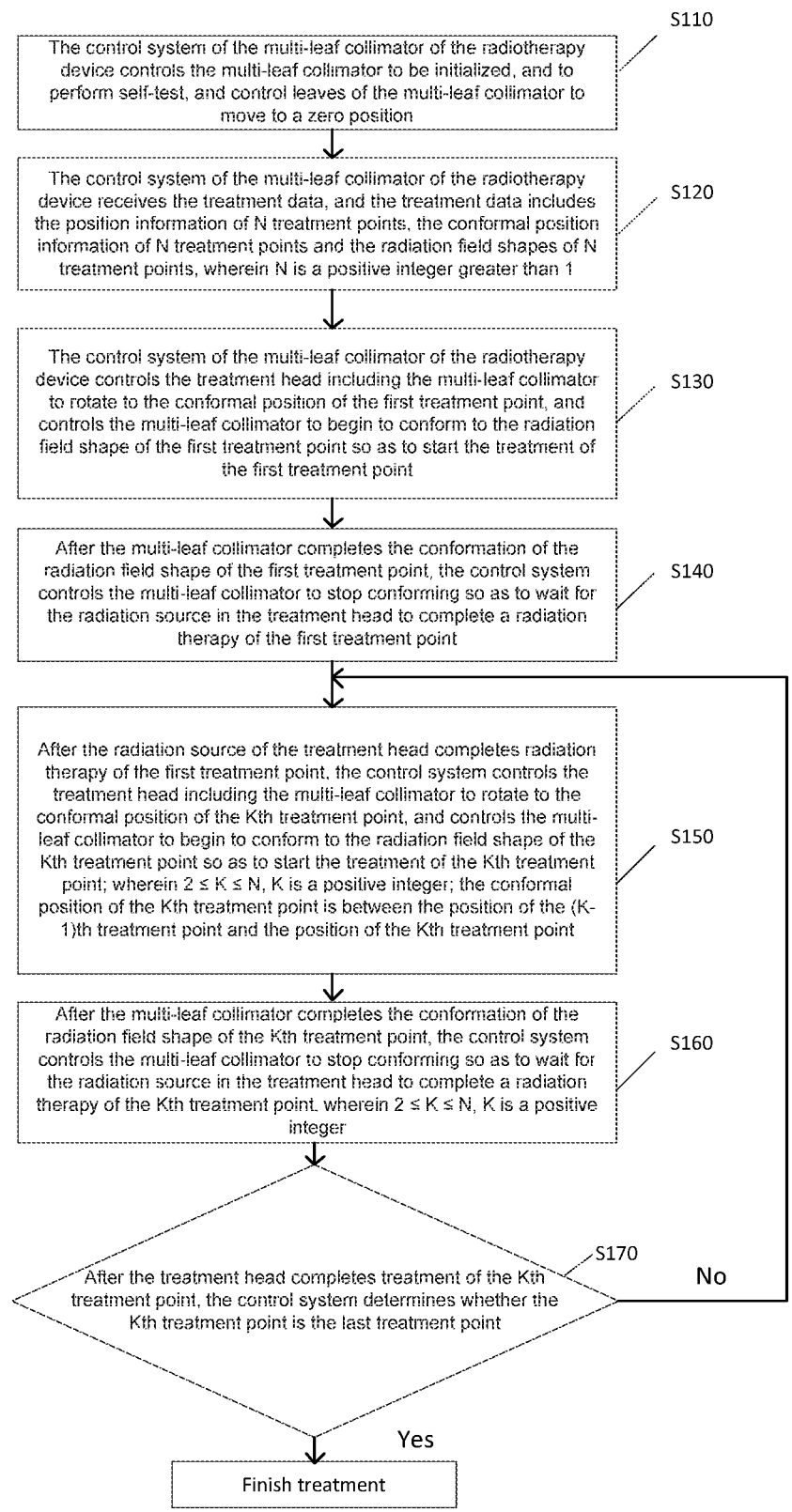
FIG. 1A is a flow diagram of a method of controlling a multi-leaf collimator provided by the present disclosure.
Figure 1B:
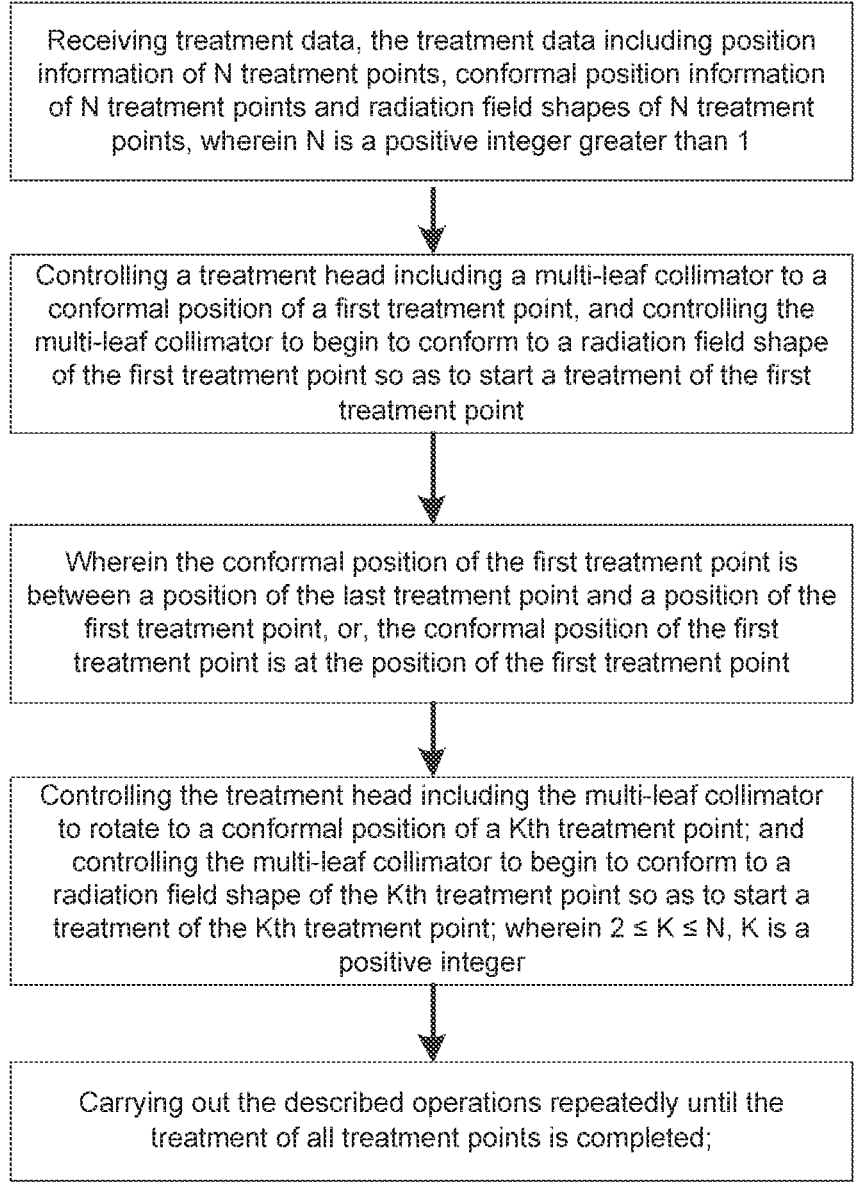
FIG. 1B is another flow diagram of a method of controlling a multi-leaf collimator provided by the present disclosure.

Referring to FIG. 1A and FIG. 1B, FIG. 1A is a flow diagram of a control method of a multi-leaf collimator provided by the present disclosure, and FIG. 1B is another flow diagram of a method of controlling a multi-leaf collimator provided by the present disclosure. The steps of the method include:

S110: the control system of the multi-leaf collimator of the radiotherapy device controls the multi-leaf collimator to be initialized, and to perform self-test, and control leaves of the multi-leaf collimator to move to a zero position.

In a case where the patient is treated with a radiotherapy device, an inspection operation should be performed first for the multi-leaf collimator of the radiotherapy device. The inspection operation includes controlling the multi-leaf collimator for initialization, self-test, and controlling leaves of the multi-leaf collimator to move to a zero position; the zero position is a position in which two sets of leaves of the multi-leaf collimator are separated, or a position in which two sets of leaves of the multi-leaf collimator are closed. At present, the results of the initialization of the multi-leaf collimator is to keep the two sets of leaves closed, in this way, before the radiotherapy equipment is conformed and the patient is treated, the safety of the device may be improved, and the mental pressure of the patient may be reduced.

In actual operation, in a case where the multi-leaf collimator is initialized, the two sets of leaves of the multi-leaf collimator may be in a closed state or in a separated state. In a case where the two sets of leaves are separated when the multi-leaf collimator is initialized, the result of the self-test is to detect that the leaves are in a separated position. The initialization of the multi-leaf collimator in a closed state, in a case of radiation leakage, is equivalent to adding a layer of radiation shielding, and the safety performance of the radiotherapy device is higher, relative to the initialization of the multi-leaf collimator in a separated state.

S120: the control system of the multi-leaf collimator of the radiotherapy device receives the treatment data, and the treatment data includes the position information of N treatment points, the conformal position information of N treatment points and the radiation field shapes of N treatment points, wherein N is a positive integer greater than 1.

After the control system of the multi-leaf collimator of the radiotherapy device completes the initialization of the multi-leaf collimator, the control system of the multi-leaf collimator controls the multi-leaf collimator to receive treatment data designated by the doctor based on the patient's condition, and the treatment data is included in a treatment plan. The treatment plan includes the patient's condition and a corresponding treatment method, for example, the prescribed time of the patient's medical treatment, the number of radiotherapy, and the situation of the treatment points during each radiotherapy process. Since the patient's condition may change dynamically during the course of radiotherapy, the preset treatment plan needs to be adjusted according to the change of the patient's condition. Once the treatment plan is completed, it will be uploaded to the software in the medical document management system. The control system of the multi-leaf collimator of the radiotherapy device in the present disclosure is connected to the software in the medical document management system to obtain treatment data of a corresponding patient.

The treatment data at least include the position information of N treatment points, the conformal position information of N treatment points and the radiation field shapes of N treatment points. In some embodiments, the radiation field shape is a two-dimensional projection shape of the lesion obtained by projecting from the position of the treatment point to the lesion. The radiation field shapes of the N treatment points included in the treatment data are data that the leaves reach the preset positions to conform to form the radiation field shapes by controlling the rotation of a motor when the multi-leaf collimator is used for conforming, that is, control data that the leaves of the multi-leaf collimator reach specific positions to form radiation field shapes. In some embodiments, the conformal position of the first treatment point is between the position of the last treatment point and the position of the first treatment point, or, the conformal position of the first treatment point is at the position of the first treatment point. The conformal position of the Kth treatment point is between the position of the (K−1)th treatment point and the position of the Kth treatment point; wherein $2 \leq K \leq N$, K is a positive integer.

In addition, the treatment data further include a treatment sequence of the treatment points, a first rotation angle and a second rotation angle of a roller during the treatment of the treatment points, and treatment time for treating the corresponding treatment points. The parsed treatment data may be set to be T1~TN, the number of the treatment points is N, and the data of each treatment point includes (Tn, An1, An2 and Sn). Tn represents a nth treatment point; An1 represents the first rotation angle of the roller at the nth treatment point, An2 represents the second rotation angle of the roller at the nth treatment point; the first rotation angle of the roller is an angle of a conformal position of the treatment head at the treatment point relative to the initial position when radiotherapy is performed on the treatment point, and the second rotation angle of the roller is an angle of a position of the treatment head at the treatment point relative to the initial position, that is, an angle formed between a connection line from the treatment head at the current position to the center of the roller when treating a current treatment point and a connection line from the treatment head at the initial position to the center of the roller; Sn represents the corresponding treatment time at the nth treatment point. In some embodiments, in a case where the roller rotates, the radiotherapy head fixedly disposed on the inner wall of the roller is moved together. The treatment head includes the multi-leaf collimator and the radiation source, and the multi-leaf collimator rotates together with the radiation source when the roller rotates.

In some embodiments, the number N of the treatment points is set to be 5, and the received treatment data at least include position information of five treatment points, conformal position information of five treatment points and radiation field shapes corresponding to five treatment points.

S130: the control system of the multi-leaf collimator of the radiotherapy device controls the treatment head including the multi-leaf collimator to rotate to the conformal position of the first treatment point, and controls the multi-leaf collimator to begin to conform to the radiation field shape of the first treatment point so as to start the treatment of the first treatment point.

After the control system of the multi-leaf collimator of the radiotherapy device obtaining the treatment data, the control system controls the roller of the radiotherapy device to start rotating, and the multi-leaf collimator of the treatment head rotates together while the roller rotates. In a case where the multi-leaf collimator in the treatment head is rotated to the conformal position of the first treatment point according to the treatment data, the control system controls the multi-leaf collimator to conform the first treatment point according to the radiation field shape of the first treatment point in the treatment data. For example, in a case where the N treatment points are arranged in a straight line, the conformal position of the first treatment point is at the position of the first treatment point. Or, for example, in a case where the N treatment points are arranged in a circular shape, the conformal position of the first treatment point is between the position of the first treatment point and the position of the last treatment points.

S140: after the multi-leaf collimator completes the conformation of the radiation field shape of the first treatment point, the control system controls the multi-leaf collimator to stop conforming so as to wait for the radiation source in the treatment head to complete a radiation therapy of the first treatment point.

In a case where the conformal position of the first treatment point is at the position of the first treatment point, whether the multi-leaf collimator completes conformation to the first treatment point may be determined based on the movement position of the two sets of leaves of the multi-leaf collimator. After the conformation is finished, the control system controls the multi-leaf collimator to stop conforming. Moreover, the control system controls the radiation source in the treatment head to perform radiation therapy of the first treatment point.

In a case where the conformal position of the first treatment point is between the position of the first treatment point and the position of the last treatment point, when the treatment head is rotated to the position of the first treatment point, the multi-leaf collimator complete the conformation of the radiation field shape of the first treatment point. At this time, the control system controls the multi-leaf collimator to stop conforming. Moreover, the control system controls the radiation source of the treatment head to perform radiation therapy of the first treatment point. That is, before or at the time the treatment head is controlled to rotate to the first treatment point, the multi-leaf collimator is controlled to complete the conformation of the first treatment point.

Two sets of leaves of the multi-leaf collimator are controlled to remain stationary or moving while the control system controls the multi-leaf collimator to stop conforming. The two sets of leaves of the multi-leaf collimator are kept in motion for dynamic intensity adjustment to adjust the dose at the treatment point.

S150: after the radiation source of the treatment head completes radiation therapy of the first treatment point, the control system controls the treatment head including the multi-leaf collimator to rotate to the conformal position of the Kth treatment point, and controls the multi-leaf collimator to begin to conform to the radiation field shape of the Kth treatment point so as to start the treatment of the Kth treatment point; wherein 2≤K≤N, K is a positive integer; the conformal position of the Kth treatment point is between the position of the (K−1)th treatment point and the position of the Kth treatment point.

Determining that the multi-leaf collimator begins to conform to the radiation field shape of the Kth treatment point in a case where the treatment head is rotated to the conformal position of the Kth treatment point. That is, it is necessary to ensure that the treatment of the (K−1)th treatment point by the radiation source of the treatment head has ended before or at the time the treatment head is controlled to rotate to the conformal position of the Kth treatment point.

In the step S150, after completing the treatment of the first treatment point, the treatment head rotates and leaves the position of the first treatment point and rotates to the conformal position of the second treatment point so as to start to conform to the second treatment point.

It should be noted that the treatment sequence of the treatment points may be determined according to the rotation angles of the roller corresponding to the treatment points in the treatment data. When the roller starts to move, a rotation angle of the roller at a position of the treatment head is set to be 0°, and in a case where an angle of the roller rotates is equal to the first rotation angle of the roller of a certain treatment point during the rotation of the treatment head with the roller, a conformal position of the certain treatment point is reached; in a case where an angle of the roller rotates is equal to the second rotation angle of the roller of a certain treatment point during the rotation of the treatment head with the roller, a position of the certain treatment point is reached. In a case where the treatment head reaches a conformal position between the first treatment point and the second treatment point, the radiation source in the treatment head completes the treatment of the first treatment point. At this time, the control system controls the multi-leaf collimator to begin to conform to a radiation field shape of the second treatment point.

And so on, in a case where the treatment head is rotated between the (K−1)th treatment point and the Kth treatment point, the radiation source of the treatment head completes the treatment of the (K−1)th treatment point. At this time, the control system controls the multi-leaf collimator to begin to conform to the radiation field shape of the Kth treatment point so as to start the treatment of the Kth treatment point, wherein 2≤K≤N, K is a positive integer.

S160, after the multi-leaf collimator completes the conformation of the radiation field shape of the Kth treatment point, the control system controls the multi-leaf collimator to stop conforming so as to wait for the radiation source in the treatment head to complete a radiation therapy of the Kth treatment point, wherein 2≤K≤N, K is a positive integer.

The multi-leaf collimator rotates to the conformal position of the Kth treatment point, and the multi-leaf collimator begin to conform to the radiation field shape of the Kth treatment point so as to start the treatment of the Kth treatment point.

Determining that the multi-leaf collimator finishes conforming the radiation field shape of the Kth treatment point in a case where the treatment head is rotated to the Kth treatment point. That is, it is necessary to ensure that the multi-leaf collimator has completed the conformity of the radiation field shape of the Kth treatment point before or at the time the treatment head reaches the position of the Kth treatment point.

It should be understood that after the multi-leaf collimator completes the conformation of the radiation field shape of the (K−1)th treatment point, and before the multi-leaf collimator begins to conform to the radiation field shape of the Kth treatment point, the multi-leaf collimator stop conforming and wait for the radiation source of the treatment head to treat the (K−1)th treatment point. That is, before or at the time the treatment head is rotated to the conformal position of the Kth treatment point, the radiation source in the treatment head has completed treatment of the (K−1)th treatment point. And, before or at the time the treatment head is rotated to the position of the Kth treatment point, controlling the multi-leaf collimator to complete the conformation of the Kth treatment point; or, after the multi-leaf collimator finishes conforming to the radiation field shape of the (K−1)th treatment point, and the multi-leaf collimator begins to conform to the radiation field shape of the Kth treatment point, the radiation source in the treatment head treats the (K−1)th treatment point.

Two sets of leaves of the multi-leaf collimator are controlled to remain stationary or moving while the control system controls the multi-leaf collimator to stop conforming. The two sets of leaves of the multi-leaf collimator are kept in motion for dynamic intensity adjustment to adjust the dose at the treatment point.

S170: after the treatment head completes treatment of the Kth treatment point, the control system determines whether the Kth treatment point is the last treatment point. If not, the control system controls the treatment head to repeatedly perform the operations of S150 and S160 until the treatment of all treatment points is completed. If yes, the treatment is ended.

In some embodiments, in the above S130 to S160, the control system monitors in real time whether the position of the treatment head is at the position of the first treatment point or the Kth treatment point. In a case where the control system monitors in real time that the treatment head reaches a conformal position of a treatment point, the control system controls the treatment head to begin to conform to the current treatment point.

It should be noted that, for a control method of a multi-leaf collimator, some of the above steps are not necessary. For example, S110 is not necessary, and in some embodiments, S110 may not be performed. For another example, S140 and S160 are not necessary.

By the control method of the multi-leaf collimator of the present disclosure, a condition that the treatment process of the radiation source and the conformal process of the multi-leaf collimator are not synchronized may be minimized, thereby reducing radiation damage to the normal parts of the patient.

Figure 2:
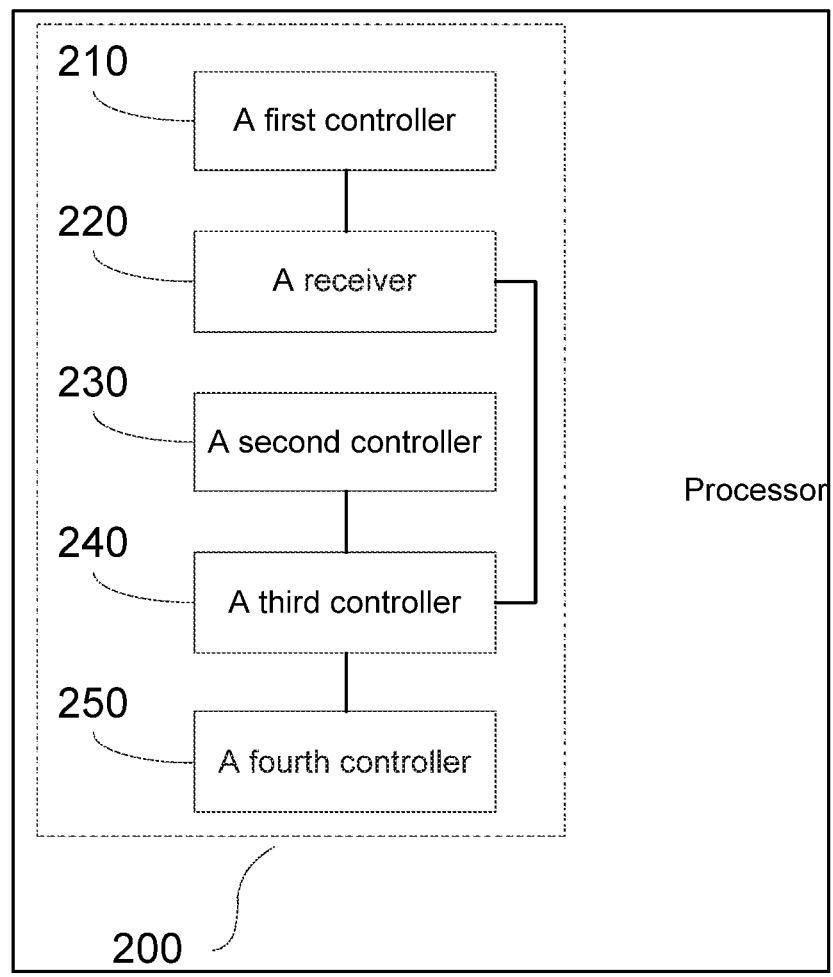
FIG. 2 is a schematic diagram showing a structure of a system of controlling a multi-leaf collimator provided by the present disclosure.
Figure 3:
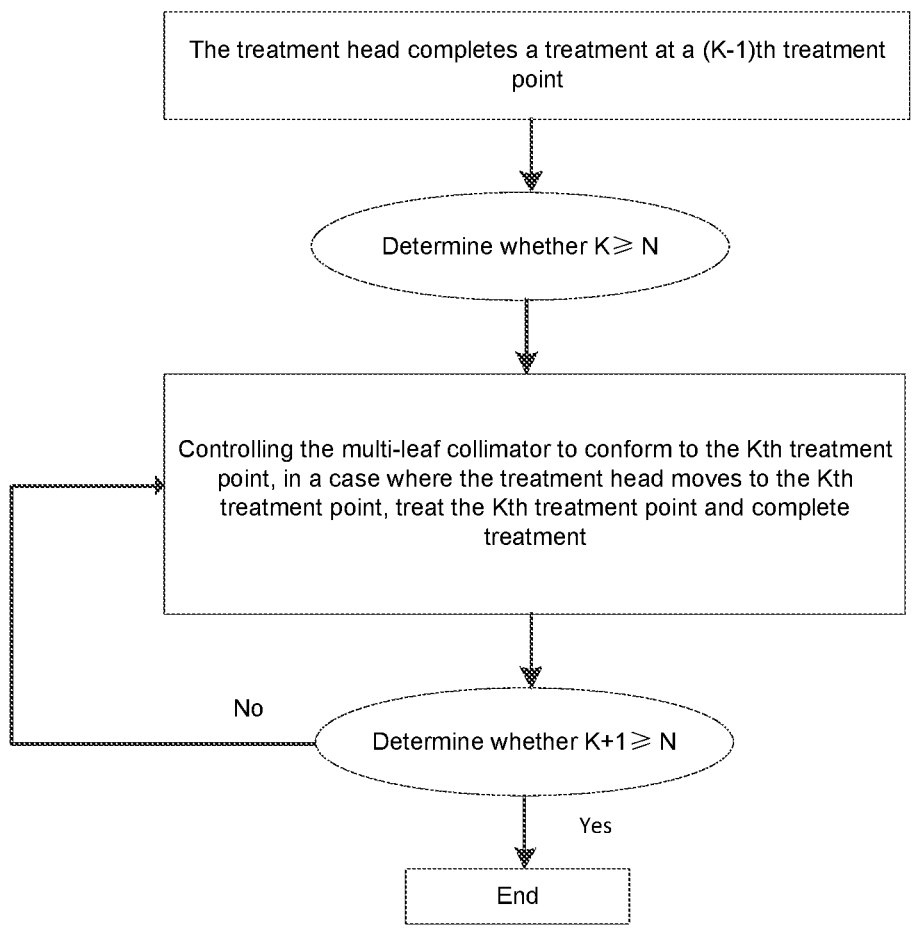
FIG. 3 is a schematic diagram of the principle of a system of controlling a multi-leaf collimator provided by the present disclosure for determining whether the Kth treatment point is the last treatment point.

Referring to FIG. 2, FIG. 2 is a schematic diagram showing a structure of a system of controlling the multi-leaf collimator provided by the present disclosure. The control system 200 includes a processor, and the processor performs various steps in the control methods of the multi-leaf collimator described above. In some embodiments, the processor includes: a first controller 210, a receiver 220, a second controller 230, a third controller 240, and a fourth controller 250. It should be noted that the first controller 210, the receiver 220, the second controller 230, the third controller 240, and the fourth controller 250 are all divisions of functional modules performed by the processor. The division of the functional modules may be implemented in a form of hardware or in a form of software. It should be noted that the foregoing division of each module is schematic, and is only divided into one logical function, and may be further divided in actual implementation.

The first controller 210 is configured to control the multi-leaf collimator to be initialized, and to perform self-test, and control two sets of leaves of the multi-leaf collimator to move to a zero position.

The receiver 220 is configured to receive the treatment data, and the treatment data includes the position information of N treatment points, the conformal position information of N treatment points and the radiation field shapes of N treatment points, wherein N is a positive integer greater than 1.

The second controller 230 is configured to control the rotation of the treatment head including the multi-leaf collimator, and the third controller 240 is configured to control the multi-leaf collimator to begin to conform to the radiation field shape of the first treatment point so as to start the treatment of the first treatment point when the second controller 230 controls the treatment head to rotate to the conformal position of the first treatment point; the control principles of the second controller 230 and the third controller 240 are similar or even the same as the first controller 210. In other embodiments of the present disclosure, the three may use the same controller, or may use different first controller 210, second controller 230, and third controller 240 respectively.

After the treatment head completes the conformation of the first treatment point, the treatment of the first treatment point begins. The fourth controller 250 is configured to control the radiation source of the treatment head to treat the first treatment point.

After the treatment head completes the treatment of the first treatment point, during the subsequent treatment, in a case where the treatment head is rotated to the position between the (K−1)th treatment point and the position of the Kth treatment point, the control system controls the multi-leaf collimator to begin to conform to the radiation field shape of the Kth treatment point and begin the treatment of the Kth treatment point when the treatment head reaches the position of the Kth treatment point; wherein 2≤K≤N, K is a positive integer.

Two sets of leaves of the multi-leaf collimator are controlled to remain stationary or moving after the multi-leaf collimator completes the conformation of the radiation field shape of the Kth treatment point. The two sets of leaves of the multi-leaf collimator are kept in motion for dynamic intensity adjustment to adjust the dose at the treatment point.

Further, the fourth controller is configured to control the radiation source in the treatment head to finish the treatment of the (K−1)th treatment points before or at the time the second controller controls the treatment head to rotate to the conformal position of the Kth treatment point.

In addition, the second controller 230 is further configured to monitor the position of the treatment head in real time. In a case where the treatment head reaches a conformal position of a treatment point, the second controller 230 controls the treatment head to begin to conform to the current treatment point.

In addition, the third controller is further configured to determine whether the Kth treatment point is the last treatment point in a case where the treatment head reaches the conformal position of the Kth treatment point. If the Kth treatment point is the last treatment point, the treatment is stopped after the treatment of the treatment point is completed; otherwise, after the treatment of the treatment point is completed, the treatment of the next treatment point is continued.

Through the present disclosure, a condition that the treatment process of the radiation source and the conformal process of the multi-leaf collimator are not synchronized may be minimized, thereby reducing radiation damage to the normal parts of the patient.

The present disclosure provides a non-transitory computer readable storage medium storing executable instructions. In a case where the executable instructions are executed by the system of controlling the multi-leaf collimator, the executable instructions make the system of controlling the multi-leaf collimator perform the methods as described in the above embodiments.

The above descriptions are only embodiments of the present disclosure, and are not intended to limit the patent scope of the present disclosure. Any equivalent structure or equivalent process transformation made by the specification and the drawings content of the present disclosure directly or indirectly used in other related technical fields, are all included in the patent protection scope of the present disclosure.

What is claimed is:

1. A method of controlling a multi-leaf collimator, comprising:

receiving treatment data, the treatment data including position information of N treatment points, conformal position information of N treatment points and radiation field shapes of N treatment points, wherein N is a positive integer greater than 1;

controlling a treatment head including the multi-leaf collimator to rotate to a conformal position of a first treatment point, and controlling the multi-leaf collimator to begin to conform to a radiation field shape of the first treatment point so as to start a treatment of the first treatment point;

wherein the conformal position of the first treatment point is between a position of a last treatment point and a position of the first treatment point, or, the conformal position of the first treatment point is at the position of the first treatment point;

controlling the treatment head including the multi-leaf collimator to rotate to a conformal position of a Kth treatment point; and controlling the multi-leaf collimator to begin to conform to a radiation field shape of the Kth treatment point so as to start a treatment of the Kth treatment point; wherein 2≤K≤N, K is a positive integer;

carrying out the above operations repeatedly until conformation of the radiation field shape and treatment of all treatment points are completed; and wherein the conformal position of the Kth treatment point is between a position of a (K-1)th treatment point and a position of the Kth treatment point.

2. The method of controlling a multi-leaf collimator according to claim 1, wherein, before receiving the treatment data, the method further includes: controlling the multi-leaf collimator to be initialized and to perform self-test, and controlling two sets of leaves of the multi-leaf collimator to move to a zero position.

3. The method of controlling a multi-leaf collimator according to claim 2, wherein the zero position is a position in which the two sets of leaves of the multi-leaf collimator are separated, or a position in which the two sets of leaves of the multi-leaf collimator are closed.

4. The method of controlling a multi-leaf collimator according to claim 1, wherein the treatment data further include a treatment sequence of the N treatment points, a rotation angle of a roller during the treatment of each of the N treatment points, and treatment time for treating each of the N treatment points; and the rotation angle of the roller is an angle formed between a connection line from the treatment head at a current position to a center of the roller when treating a current treatment point and a connection line from the treatment head at a initial position to the center of the roller.

5. The method of controlling a multi-leaf collimator according to claim 1, wherein, after controlling the multi-leaf collimator to complete the conformation of the radiation field shape of the (K-1)th treatment point, and before controlling the multi-leaf collimator to begin to conform the radiation field shape of the Kth treatment point, the method further comprises:

controlling the multi-leaf collimator to stop conforming so as to wait for a radiation source of the treatment head to complete a treatment of the (K-1)th treatment point.

6. The method of controlling a multi-leaf collimator according to claim 5, further comprising:

monitoring in real time whether the position of the treatment head is at a conformal position of the first treatment point or the Kth treatment point.

7. The method of controlling a multi-leaf collimator according to claim 5, wherein, while controlling the multi-leaf collimator to stop conforming, the method further comprises: controlling two sets of leaves in the multi-leaf collimator to remain stationary.

8. The method of controlling a multi-leaf collimator according to claim 5, wherein, while controlling the multi-leaf collimator to stop conforming, the method further comprises: controlling two sets of leaves in the multi-leaf collimator to move.

9. The method of controlling a multi-leaf collimator according to claim 1, wherein, before or at the time the treatment head is controlled to rotate to a conformal position of the Kth treatment point, a radiation source of the treatment head has completed the treatment of the (K-1)th treatment point;

wherein, the method further comprises:

before or at the time the treatment head is controlled to rotate to a position of the Kth treatment point, the radiation source of the treatment head is controlled to complete the conformation of the Kth treatment point.

10. The method of controlling a multi-leaf collimator according to claim 1, further comprising: determining if the Kth treatment point is the last treatment point.

11. A system of controlling a multi-leaf collimator, comprising a processor, wherein the processor is configured to perform the method of controlling the multi-leaf collimator according to claim 1.

12. A non-transitory computer readable storage medium storing executable instructions, wherein in a case where the executable instructions are executed by a system of controlling the multi-leaf collimator, the executable instructions make the system of controlling the multi-leaf collimator perform the method according to claim 1.

* * * * *